(12) United States Patent
Marczyk

(10) Patent No.: US 9,364,232 B2
(45) Date of Patent: *Jun. 14, 2016

(54) TISSUE STOP FOR SURGICAL INSTRUMENT

(71) Applicant: Covidien LP, Mansfield, MA (US)

(72) Inventor: Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/805,593

(22) Filed: Jul. 22, 2015

(65) Prior Publication Data

US 2015/0320421 A1     Nov. 12, 2015

Related U.S. Application Data

(63) Continuation of application No. 13/493,346, filed on Jun. 11, 2012, now Pat. No. 9,107,664, which is a continuation of application No. 12/952,371, filed on Nov. 23, 2010, now Pat. No. 8,215,532, which is a (Continued)

(51) Int. Cl.
*A61B 17/068*    (2006.01)
*A61B 17/072*    (2006.01)

(Continued)

(52) U.S. Cl.
CPC ......... *A61B 17/07207* (2013.01); *A61B 17/072* (2013.01); *A61B 18/1442* (2013.01); *A61B 2017/07221* (2013.01);

(Continued)

(58) Field of Classification Search
CPC ............. A61B 17/068; A61B 17/0686; A61B 17/072; A61B 17/07207
USPC ............................................ 227/175.1, 176.1
See application file for complete search history.

(56) References Cited

U.S. PATENT DOCUMENTS

| | | | |
|---|---|---|---|
| 3,017,637 A | 1/1962 | Sampson | |
| 3,079,606 A | 3/1963 | Bobrov et al. | |

(Continued)

FOREIGN PATENT DOCUMENTS

| | | | |
|---|---|---|---|
| AU | 5476586 A | 9/1986 | |
| CA | 2773414 A1 | 11/2012 | |

(Continued)

OTHER PUBLICATIONS

Japanese Office Action dated Oct. 22, 2015, issued in Japanese Application No. 2011-194158.

(Continued)

*Primary Examiner* — Michelle Lopez

(57) ABSTRACT

A surgical instrument including a handle assembly, an elongated portion, an end effector, and a stop member is disclosed. The end effector is disposed adjacent a distal portion of the elongated portion and includes a first jaw member and a second jaw member. At least one jaw member is movable with respect to the other jaw member between spaced and approximated positions. The first jaw member includes an upper tissue-contacting surface and a lower shelf portion. The shelf portion includes a groove disposed therein. The stop member is disposed adjacent a distal portion of the first jaw member and is pivotable with respect to the first jaw member between a first position, a significant portion of the stop member being positioned external to the first jaw member, and a second position where a lower portion of the stop member being positioned at least partially within the groove.

10 Claims, 13 Drawing Sheets

Related U.S. Application Data continuation-in-part of application No. 12/759,897, filed on Apr. 14, 2010, now Pat. No. 8,360,298, which is a continuation-in-part of application No. 12/553,174, filed on Sep. 3, 2009, now Pat. No. 7,988,028, which is a continuation-in-part of application No. 12/235,751, filed on Sep. 23, 2008, now Pat. No. 7,896,214.

(51) Int. Cl.
*A61B 18/14* (2006.01)
*A61B 17/29* (2006.01)
*A61B 17/32* (2006.01)
*A61B 19/00* (2006.01)

(52) U.S. Cl.
CPC ............ *A61B 2017/07271* (2013.01); *A61B 2017/07278* (2013.01); *A61B 2017/07285* (2013.01); *A61B 2017/2945* (2013.01); *A61B 2017/320052* (2013.01); *A61B 2018/1432* (2013.01); *A61B 2019/303* (2013.01); *A61B 2090/033* (2016.02)

(56) References Cited

U.S. PATENT DOCUMENTS

| | | |
|---|---|---|
| 3,490,675 A | 1/1970 | Green et al. |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,881,544 A | 11/1989 | Green et al. |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,008 A | 11/1995 | Rodak |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A * | 1/1996 | Green .............. A61B 17/0686 227/175.1 |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |

(56) References Cited

U.S. PATENT DOCUMENTS

| | | | |
|---|---|---|---|
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A * | 9/1997 | Yoon .................. A61B 17/072 227/176.1 |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,954,736 A | 9/1999 | Bishop et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |

(56) References Cited

U.S. PATENT DOCUMENTS

| | | |
|---|---|---|
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,724 B2 | 11/2007 | Green et al. |
| 7,296,772 B2 | 11/2007 | Wang |
| 7,300,444 B1 | 11/2007 | Nielsen et al. |
| 7,303,108 B2 | 12/2007 | Shelton, IV |
| 7,308,998 B2 | 12/2007 | Mastri et al. |
| 7,328,828 B2 | 2/2008 | Ortiz et al. |
| 7,328,829 B2 | 2/2008 | Arad et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,399,310 B2 | 7/2008 | Edoga et al. |
| 7,401,720 B1 | 7/2008 | Durrani |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,495 B2 | 9/2008 | Menn et al. |
| 7,422,139 B2 | 9/2008 | Shelton, IV et al. |
| 7,431,189 B2 | 10/2008 | Shelton, IV et al. |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,458,494 B2 | 12/2008 | Matsutani et al. |
| 7,462,185 B1 | 12/2008 | Knodel |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,473,258 B2 | 1/2009 | Clauson et al. |
| 7,896,214 B2 * | 3/2011 | Farascioni ........ A61B 17/07207 227/175.1 |
| 7,988,028 B2 * | 8/2011 | Farascioni ........ A61B 17/07207 227/175.1 |
| 8,215,532 B2 * | 7/2012 | Marczyk .......... A61B 17/07207 227/175.1 |
| 8,360,298 B2 * | 1/2013 | Farascioni ........ A61B 17/07207 227/176.1 |
| 9,107,664 B2 * | 8/2015 | Marczyk .......... A61B 17/07207 |
| 2002/0004498 A1 | 1/2002 | Doherty et al. |
| 2002/0009193 A1 | 1/2002 | Deguchi |
| 2002/0018323 A1 | 2/2002 | Li et al. |
| 2002/0032948 A1 | 3/2002 | Ahn et al. |
| 2002/0036748 A1 | 3/2002 | Chapoy et al. |
| 2002/0045442 A1 | 4/2002 | Silen et al. |
| 2002/0069595 A1 | 6/2002 | Knudson et al. |
| 2002/0084304 A1 | 7/2002 | Whitman |

(56) References Cited

U.S. PATENT DOCUMENTS

| | | |
|---|---|---|
| 2002/0111621 A1 | 8/2002 | Wallace et al. |
| 2002/0143346 A1 | 10/2002 | McGuckin et al. |
| 2002/0177843 A1 | 11/2002 | Anderson et al. |
| 2002/0188294 A1 | 12/2002 | Couture et al. |
| 2002/0190093 A1 | 12/2002 | Fenton |
| 2003/0009193 A1 | 1/2003 | Corsaro |
| 2003/0105476 A1 | 6/2003 | Sancoff et al. |
| 2003/0132268 A1 | 7/2003 | Whitman |
| 2004/0004105 A1 | 1/2004 | Jankowski |
| 2004/0007608 A1 | 1/2004 | Ehrenfels et al. |
| 2004/0050902 A1 | 3/2004 | Green et al. |
| 2004/0082952 A1 | 4/2004 | Dycus et al. |
| 2004/0093029 A1 | 5/2004 | Zubik et al. |
| 2004/0094597 A1 | 5/2004 | Whitman et al. |
| 2004/0108357 A1 | 6/2004 | Milliman et al. |
| 2004/0149802 A1 | 8/2004 | Whitman |
| 2004/0173659 A1 | 9/2004 | Green et al. |
| 2004/0199180 A1 | 10/2004 | Knodel et al. |
| 2004/0199181 A1 | 10/2004 | Knodel et al. |
| 2004/0232199 A1 | 11/2004 | Shelton et al. |
| 2004/0232200 A1 | 11/2004 | Shelton et al. |
| 2004/0232201 A1 | 11/2004 | Wenchell et al. |
| 2004/0243151 A1 | 12/2004 | Demmy et al. |
| 2004/0267310 A1 | 12/2004 | Racenet et al. |
| 2004/0267311 A1 | 12/2004 | Viola et al. |
| 2005/0006429 A1 | 1/2005 | Wales et al. |
| 2005/0006430 A1 | 1/2005 | Wales |
| 2005/0006431 A1 | 1/2005 | Shelton et al. |
| 2005/0006432 A1 | 1/2005 | Racenet et al. |
| 2005/0006433 A1 | 1/2005 | Milliman et al. |
| 2005/0006434 A1 | 1/2005 | Wales et al. |
| 2005/0023324 A1 | 2/2005 | Doll et al. |
| 2005/0023325 A1 | 2/2005 | Gresham et al. |
| 2005/0067457 A1 | 3/2005 | Shelton et al. |
| 2005/0067458 A1 | 3/2005 | Swayze et al. |
| 2005/0067459 A1 | 3/2005 | Swayze et al. |
| 2005/0067460 A1 | 3/2005 | Milliman et al. |
| 2005/0070758 A1 | 3/2005 | Wells et al. |
| 2005/0070925 A1 | 3/2005 | Shelton et al. |
| 2005/0070958 A1 | 3/2005 | Swayze et al. |
| 2005/0072827 A1 | 4/2005 | Mollenauer |
| 2005/0082336 A1 | 4/2005 | Ivanko |
| 2005/0103819 A1 | 5/2005 | Racenet et al. |
| 2005/0119669 A1 | 6/2005 | Demmy |
| 2005/0127131 A1 | 6/2005 | Mastri et al. |
| 2005/0145671 A1 | 7/2005 | Viola |
| 2005/0159778 A1 | 7/2005 | Heinrich et al. |
| 2005/0165415 A1 | 7/2005 | Wales |
| 2005/0173490 A1 | 8/2005 | Shelton |
| 2005/0178813 A1 | 8/2005 | Swayze et al. |
| 2005/0184121 A1 | 8/2005 | Heinrich |
| 2005/0184123 A1 | 8/2005 | Scirica |
| 2005/0184124 A1 | 8/2005 | Scirica et al. |
| 2005/0184125 A1 | 8/2005 | Marczyk |
| 2005/0184126 A1 | 8/2005 | Green et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0230453 A1 | 10/2005 | Viola |
| 2005/0247753 A1* | 11/2005 | Kelly ................ A61B 17/072 227/176.1 |
| 2005/0263562 A1 | 12/2005 | Shelton et al. |
| 2005/0279804 A1 | 12/2005 | Scirica et al. |
| 2006/0000867 A1 | 1/2006 | Shelton et al. |
| 2006/0000868 A1 | 1/2006 | Shelton et al. |
| 2006/0011699 A1 | 1/2006 | Olson et al. |
| 2006/0016853 A1 | 1/2006 | Racenet |
| 2006/0022014 A1 | 2/2006 | Shelton et al. |
| 2006/0022015 A1 | 2/2006 | Shelton et al. |
| 2006/0025809 A1 | 2/2006 | Shelton |
| 2006/0043147 A1 | 3/2006 | Mastri et al. |
| 2006/0049229 A1 | 3/2006 | Milliman et al. |
| 2006/0049230 A1 | 3/2006 | Shelton et al. |
| 2006/0060630 A1 | 3/2006 | Shelton et al. |
| 2006/0081678 A1 | 4/2006 | Ehrenfels et al. |
| 2006/0097026 A1 | 5/2006 | Shelton |
| 2006/0124688 A1 | 6/2006 | Racenet et al. |
| 2006/0124689 A1 | 6/2006 | Arad et al. |
| 2006/0138193 A1 | 6/2006 | Viola et al. |
| 2006/0138194 A1 | 6/2006 | Viola et al. |
| 2006/0151567 A1 | 7/2006 | Roy |
| 2006/0151568 A1 | 7/2006 | Weller et al. |
| 2006/0151569 A1 | 7/2006 | Ehrenfels et al. |
| 2006/0163312 A1* | 7/2006 | Viola ................ A61B 17/072 227/175.1 |
| 2006/0175375 A1 | 8/2006 | Shelton et al. |
| 2006/0180634 A1 | 8/2006 | Shelton et al. |
| 2006/0201990 A1 | 9/2006 | Mastri et al. |
| 2006/0201991 A1 | 9/2006 | Mastri et al. |
| 2006/0226195 A1 | 10/2006 | Scirica et al. |
| 2006/0226196 A1 | 10/2006 | Hueil et al. |
| 2006/0255090 A1 | 11/2006 | Milliman et al. |
| 2006/0271038 A1 | 11/2006 | Johnson et al. |
| 2006/0278680 A1 | 12/2006 | Viola et al. |
| 2006/0278681 A1 | 12/2006 | Viola et al. |
| 2006/0289600 A1 | 12/2006 | Wales et al. |
| 2006/0289602 A1 | 12/2006 | Wales et al. |
| 2007/0023477 A1 | 2/2007 | Whitman et al. |
| 2007/0027469 A1 | 2/2007 | Smith et al. |
| 2007/0034669 A1 | 2/2007 | de la Torre et al. |
| 2007/0034670 A1 | 2/2007 | Racenet et al. |
| 2007/0045379 A1 | 3/2007 | Shelton |
| 2007/0045380 A1 | 3/2007 | Mastri et al. |
| 2007/0068989 A1 | 3/2007 | Shelton |
| 2007/0068990 A1 | 3/2007 | Shelton et al. |
| 2007/0073340 A1 | 3/2007 | Shelton et al. |
| 2007/0073341 A1 | 3/2007 | Smith et al. |
| 2007/0075114 A1 | 4/2007 | Shelton et al. |
| 2007/0075115 A1 | 4/2007 | Olson et al. |
| 2007/0075116 A1 | 4/2007 | Whitman |
| 2007/0083233 A1 | 4/2007 | Ortiz et al. |
| 2007/0083234 A1 | 4/2007 | Shelton et al. |
| 2007/0084896 A1 | 4/2007 | Doll et al. |
| 2007/0084897 A1 | 4/2007 | Shelton et al. |
| 2007/0084898 A1 | 4/2007 | Scirica |
| 2007/0084899 A1 | 4/2007 | Taylor |
| 2007/0102472 A1 | 5/2007 | Shelton |
| 2007/0102473 A1 | 5/2007 | Shelton et al. |
| 2007/0102474 A1 | 5/2007 | Shelton et al. |
| 2007/0102475 A1 | 5/2007 | Ortiz et al. |
| 2007/0102476 A1 | 5/2007 | Shelton et al. |
| 2007/0106317 A1 | 5/2007 | Shelton et al. |
| 2007/0108252 A1 | 5/2007 | Racenet et al. |
| 2007/0114261 A1 | 5/2007 | Ortiz et al. |
| 2007/0114262 A1 | 5/2007 | Mastri et al. |
| 2007/0119900 A1 | 5/2007 | Ehrenfels et al. |
| 2007/0119901 A1 | 5/2007 | Ehrenfels et al. |
| 2007/0125826 A1 | 6/2007 | Shelton |
| 2007/0125827 A1 | 6/2007 | Viola |
| 2007/0125828 A1 | 6/2007 | Rethy et al. |
| 2007/0145095 A1 | 6/2007 | Heinrich et al. |
| 2007/0145096 A1 | 6/2007 | Viola et al. |
| 2007/0152014 A1 | 7/2007 | Gillum et al. |
| 2007/0158385 A1 | 7/2007 | Hueil et al. |
| 2007/0170225 A1 | 7/2007 | Shelton et al. |
| 2007/0175947 A1 | 8/2007 | Ortiz et al. |
| 2007/0175948 A1 | 8/2007 | Scirica et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175952 A1 | 8/2007 | Shelton et al. |
| 2007/0175953 A1 | 8/2007 | Shelton et al. |
| 2007/0175954 A1 | 8/2007 | Viola |
| 2007/0175955 A1 | 8/2007 | Shelton et al. |
| 2007/0175956 A1 | 8/2007 | Swayze et al. |
| 2007/0175957 A1 | 8/2007 | Shelton et al. |
| 2007/0175958 A1 | 8/2007 | Shelton et al. |
| 2007/0175959 A1 | 8/2007 | Shelton et al. |
| 2007/0175960 A1 | 8/2007 | Shelton et al. |
| 2007/0175961 A1 | 8/2007 | Shelton et al. |
| 2007/0175962 A1 | 8/2007 | Shelton et al. |
| 2007/0175964 A1 | 8/2007 | Shelton et al. |
| 2007/0179528 A1 | 8/2007 | Soltz et al. |
| 2007/0187453 A1 | 8/2007 | Smith et al. |

(56) References Cited

U.S. PATENT DOCUMENTS

| | | |
|---|---|---|
| 2007/0187454 A1 | 8/2007 | Scirica |
| 2007/0187455 A1 | 8/2007 | Demmy et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0278277 A1 | 12/2007 | Wixey et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0048002 A1 | 2/2008 | Smith et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0110958 A1 | 5/2008 | McKenna et al. |
| 2008/0110961 A1 | 5/2008 | Voegele et al. |
| 2008/0125812 A1 | 5/2008 | Zubik et al. |
| 2008/0149685 A1 | 6/2008 | Smith et al. |
| 2008/0164296 A1 | 7/2008 | Shelton et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0237298 A1 | 10/2008 | Schall et al. |
| 2008/0277447 A1 | 11/2008 | Smith et al. |
| 2008/0283570 A1 | 11/2008 | Boyden et al. |
| 2008/0283571 A1 | 11/2008 | Boyden et al. |
| 2008/0283572 A1 | 11/2008 | Boyden et al. |
| 2008/0283574 A1 | 11/2008 | Boyden et al. |
| 2008/0283576 A1 | 11/2008 | Boyden et al. |
| 2008/0283577 A1 | 11/2008 | Boyden et al. |
| 2008/0287987 A1 | 11/2008 | Boyden et al. |
| 2008/0296343 A1 | 12/2008 | Schall et al. |
| 2008/0296344 A1 | 12/2008 | Cropper et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0302854 A1 | 12/2008 | Rethy et al. |
| 2008/0308601 A1 | 12/2008 | Timm et al. |
| 2008/0308602 A1 | 12/2008 | Timm et al. |
| 2008/0308603 A1 | 12/2008 | Shelton et al. |
| 2008/0308604 A1 | 12/2008 | Timm et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001130 A1 | 1/2009 | Hess et al. |
| 2009/0005808 A1 | 1/2009 | Hess et al. |
| 2009/0008424 A1 | 1/2009 | Green |
| 2010/0072257 A1 | 3/2010 | Farascioni |
| 2010/0072258 A1 | 3/2010 | Farascioni et al. |
| 2010/0213238 A1 | 8/2010 | Farascioni et al. |
| 2012/0138660 A1 | 6/2012 | Shelton, IV |

FOREIGN PATENT DOCUMENTS

| | | |
|---|---|---|
| CN | 1947663 A | 4/2007 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0 324 166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537498 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1550410 A2 | 7/2005 |
| EP | 1813209 A1 | 8/2007 |
| EP | 1908413 A1 | 4/2008 |
| EP | 1915953 A1 | 4/2008 |
| EP | 2014243 A2 | 1/2009 |
| EP | 2090253 A2 | 8/2009 |
| EP | 2090254 A2 | 8/2009 |
| EP | 2116193 A1 | 11/2009 |
| EP | 2165662 A1 | 3/2010 |
| EP | 2583630 A2 | 4/2013 |
| EP | 2586382 A2 | 5/2013 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51-149985 | 12/1976 |

(56) References Cited

FOREIGN PATENT DOCUMENTS

| | | | |
|---|---|---|---|
| JP | 8-289895 A | | 11/1996 |
| SU | 659146 | A1 | 4/1979 |
| SU | 728848 | A1 | 4/1980 |
| SU | 980703 | A1 | 12/1982 |
| SU | 990220 | A1 | 1/1983 |
| WO | 8302247 | | 7/1983 |
| WO | 89/10094 | A1 | 11/1989 |
| WO | 9210976 | A1 | 7/1992 |
| WO | 9308754 | A1 | 5/1993 |
| WO | 9314706 | A1 | 8/1993 |
| WO | 03022133 | A2 | 3/2003 |
| WO | 2004032761 | A1 | 4/2004 |

OTHER PUBLICATIONS

European Search Report for EP 09252249.9-1269 date of completion is Nov. 18, 2009 (3 pages).
European Search Report for EP 11 25 0757.9-2310 date of completion is Feb. 7, 2012 (3 pages).
European Search Report for EP 11250468.3-2319 date of completion is Aug. 10, 2011 (3 pages).
European Search Report for EP 1025188.6-1269 date of completion is Feb. 25, 2011.
European Search Report dated Aug. 22, 2013 in European Application No. 13175397.
European Search Report dated Aug. 5, 2013 in European Application No. 11250785.
European Search Report EP 10251545.9 dated Jan. 2, 2014.
Chinese Office Action dated Apr. 1, 2015, issued in Chinese Application No. 2014100014945.
Japanese Office Action dated Apr. 16, 2015 issued in Japanese Appin. No. 2011-194158.
European Examination Report dated Apr. 24, 2015, issued in European Appin. No. 13155608.
Australian Office Action dated Sep. 18, 2015, issued in Australian Application No. 2013263862.
Australian Office Action dated Sep. 18, 2015, issued in Australian Application No. 2013219226.
Canadian Office Action dated Aug. 11, 2015, issued in Canadian Application No. 2,676,307.

\* cited by examiner

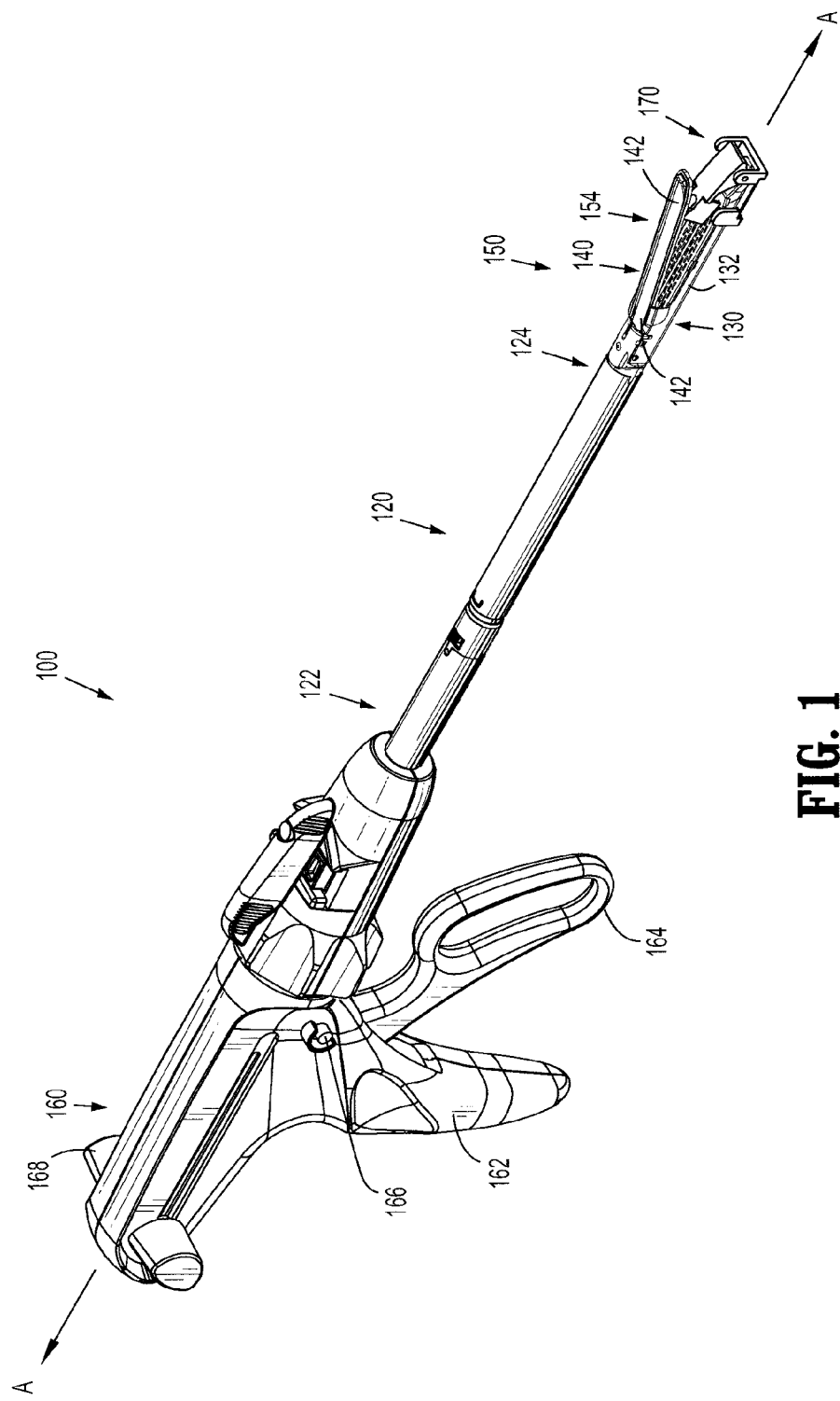

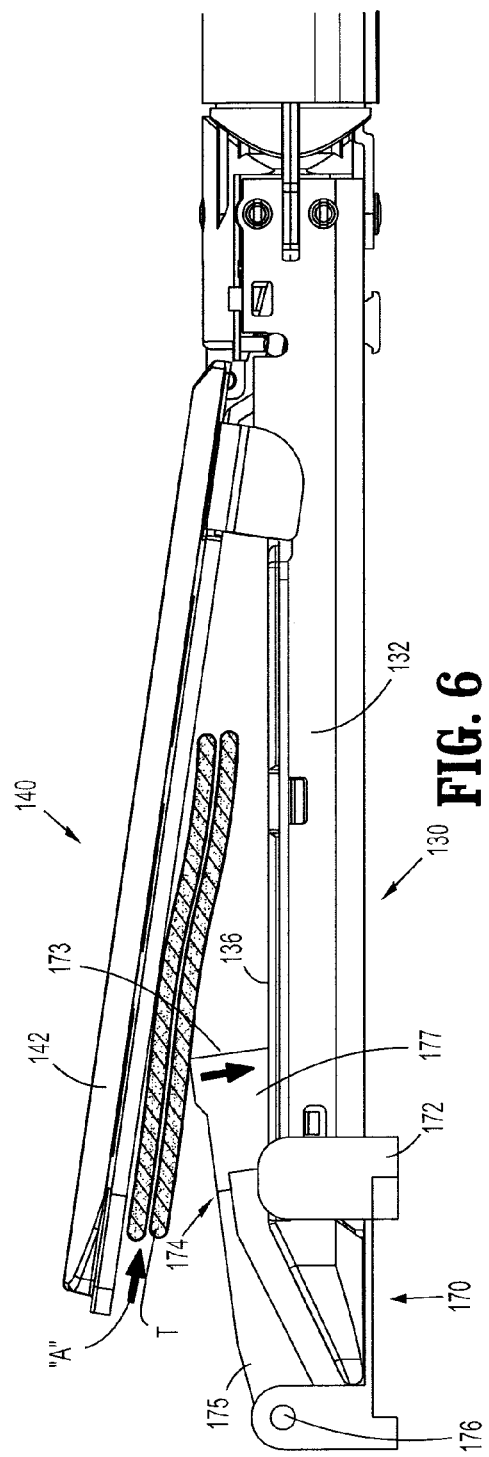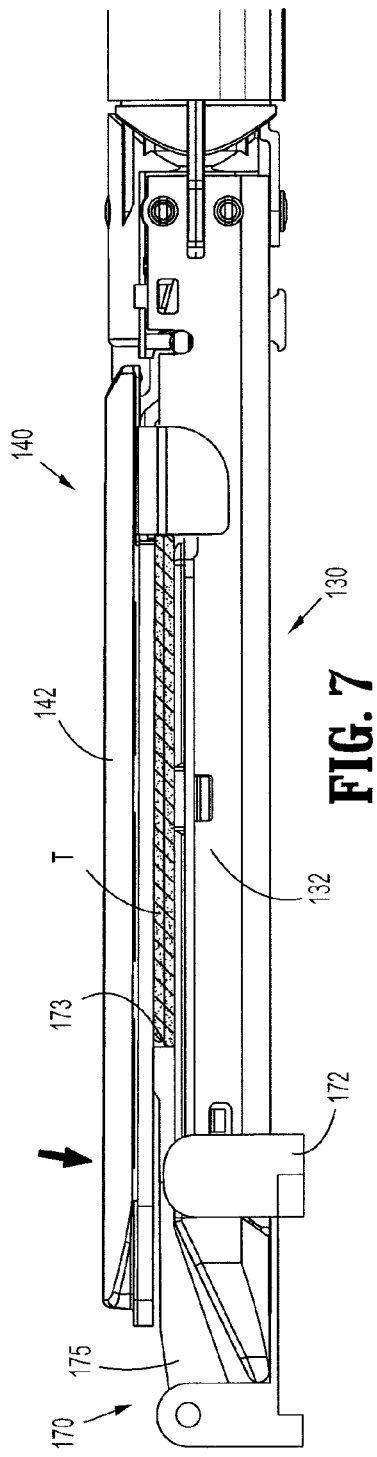

TISSUE STOP FOR SURGICAL INSTRUMENT

CROSS-REFERENCE TO RELATED APPLICATIONS

The present application is a Continuation of U.S. patent application Ser. No. 13/493,346, filed Jun. 11, 2012, which is a Continuation of U.S. patent application Ser. No. 12/952,371, filed Nov. 23, 2010, now U.S. Pat. No. 8,215,532, which is a Continuation-In-Part of U.S. patent application Ser. No. 12/759,897, filed Apr. 14, 2010, now U.S. Pat. No. 8,360,298, which is a Continuation-In-Part of U.S. patent application Ser. No. 12/553,174, filed Sep. 3, 2009, now U.S. Pat. No. 7,988,028, which is a Continuation-In-Part and claims benefit of, and claims priority to U.S. patent application Ser. No. 12/235,751, filed Sep. 23, 2008, now U.S. Pat. No. 7,896,214. The entire contents of this application are incorporated herein by reference.

BACKGROUND

1. Technical Field

The present disclosure relates generally to surgical instruments and, more specifically, to surgical instruments for surgically joining tissue.

2. Background of Related Art

Surgical stapling instruments used for applying parallel rows of staples through compressed living tissue are well known in the art. These surgical instruments are commonly employed for closing tissue or organs prior to transaction or resection, for occluding organs in thoracic and abdominal procedures, and for fastening tissue in anastomoses.

Typically, such surgical stapling instruments include an anvil assembly, a cartridge assembly for supporting an array of surgical staples, an approximation mechanism for approximating the anvil and cartridge and anvil assemblies, and a firing mechanism for ejecting the surgical staples from the cartridge assembly.

In use, a surgeon generally initially approximates the anvil and cartridge members. Next, the surgeon can fire the instrument to place staples in tissue. Additionally, the surgeon may use the same instrument or a separate instrument to cut the tissue adjacent or between the row(s) of staples. Alternatively, the surgical stapling instrument can sequentially eject the staples while the anvil and cartridge are approximated.

SUMMARY

The present disclosure relates to a surgical instrument including a handle assembly, an elongated portion, an end effector, and a stop member. The elongated portion extends distally from the handle assembly. The end effector is disposed adjacent a distal portion of the elongated portion and includes a first jaw member and a second jaw member. At least one jaw member is movable with respect to the other jaw member between spaced and approximated positions. The first jaw member includes an upper tissue-contacting surface and a lower shelf portion. The shelf portion includes a groove disposed therein. The stop member is disposed adjacent a distal portion of the first jaw member and is pivotable with respect to the first jaw member between a first position, a significant portion of the stop member being positioned external to the first jaw member, and a second position where a lower portion of the stop member being positioned at least partially within the groove.

In certain embodiments, the cartridge is curved with respect to the longitudinal axis. A biasing member may be provided and disposed in mechanical cooperation with the stop member, wherein the biasing member biases stop member towards its first position. The stop member can be pivotally coupled to the first jaw member.

In certain embodiments, the first jaw member includes a knife channel. The stop member can have a first leg and a second leg, the first leg and the second leg being positioned on opposite sides of the knife channel.

In certain desirable embodiments, a sled is translatable along the shelf of the first jaw member. The sled can include a plurality of cam wedges, and wherein each cam wedge is connected to an adjacent cam wedge by a transversely-disposed connecting member. The connecting member can be disposed adjacent a proximal portion of the sled. A distal portion each of the cam wedges can cantileveredly extend from the connecting member. The wedges may extend from the connecting member and define a space in which the stop member is disposed when the sled is disposed at the distal end of the first jaw member.

In certain embodiments, the instrument includes a beam assembly for pushing the sled toward the distal end of the first jaw member, the beam assembly having a notch, the connecting member of the sled being in engagement with the beam assembly at the notch.

The present disclosure also relates to a tool assembly for use with a surgical instrument. The tool assembly comprises an end effector and a stop member. The end effector includes a first jaw member and a second jaw member, at least one jaw member is movable with respect to the other jaw member between spaced and approximated positions. The first jaw member includes an upper tissue-contacting surface and a lower shelf portion. The shelf portion includes a groove disposed therein. The stop member is disposed adjacent a distal portion of the first jaw member and is pivotable with respect to the first jaw member between a first position wherein at least a portion of the stop member is positioned external to the first jaw member, and a second position wherein at least a portion of the stop member is positioned within the groove. The relative movement of the jaw members toward the approximated position causes at least a portion of the stop member to move toward the first jaw member.

In certain embodiments, the cartridge of the tool assembly is curved with respect to the longitudinal axis. A biasing member may be provided and disposed in mechanical cooperation with the stop member, wherein the biasing member biases stop member towards its first position. The stop member can be pivotally coupled to the first jaw member.

In certain embodiments, the first jaw member of the tool assembly includes a knife channel. The stop member can have a first leg and a second leg, the first leg and the second leg being positioned on opposite sides of the knife channel.

In certain embodiments, the tool assembly had a sled which is translatable along the shelf of the first jaw member. The sled can include a plurality of cam wedges, and wherein each cam wedge is connected to an adjacent cam wedge by a transversely-disposed connecting member. The connecting member can be disposed adjacent a proximal portion of the sled. A distal portion each of the cam wedges can cantileveredly extend from the connecting member. The wedges may extend from the connecting member and define a space in which the stop member is disposed when the sled is disposed at the distal end of the first jaw member.

In certain embodiments, the tool assembly includes a beam assembly for pushing the sled toward the distal end of the first jaw member, the beam assembly having a notch, the connecting member of the sled being in engagement with the beam assembly at the notch.

In a further aspect of the disclosure, a surgical instrument includes a handle assembly, an elongated portion, an end effector, and a stop member. The elongated portion extends distally from the handle assembly. The end effector is disposed adjacent a distal portion of the elongated portion and includes a first jaw member and a second jaw member. At least one jaw member is movable with respect to the other jaw member between spaced and approximated positions. The first jaw member includes an upper tissue-contacting surface and a lower shelf portion. The stop member is disposed adjacent a distal portion of the first jaw member and is pivotable with respect to the first jaw member between a first position, a significant portion of the stop member being positioned external to the first jaw member. The instrument also comprises a sled translatable along the shelf portion of the first jaw member, the sled including a connecting member disposed at a proximal portion of the sled, and a beam assembly for pushing the sled distally the beam assembly having a notch and the connecting member being disposed in the notch, the sled defining a space for receiving the stop member when the sled is disposed at the distal portion of the first jaw member.

The shelf portion of the first jaw member may include a groove disposed therein for receiving a portion of the stop member. The first jaw member desirably includes a knife channel. The stop member may have two legs positioned on opposite sides of the knife channel.

In another aspect of the present disclosure, a loading unit has a first jaw member including an upper tissue-contacting surface and a lower shelf portion. The shelf portion includes a groove disposed therein. A stop member is disposed adjacent a distal portion of the first jaw member and is pivotable with respect to the first jaw member between a first position wherein at least a portion of the stop member is positioned external to the first jaw member, and a second position wherein at least a portion of the stop member is positioned within the groove. The stop member is pivotably mounted so that at least a portion of the stop member can move toward the first jaw member. In certain embodiments, the stop member has two legs for receiving a knife member included in the loading unit. The loading unit may also include a sled having a connecting member at a proximal portion thereof. In certain embodiments, the sled defines a space for receiving the stop member when the sled is disposed at the distal portion of the first jaw member. The loading unit may include a beam assembly, the beam assembly being connected to the sled at the connecting member.

BRIEF DESCRIPTION OF FIGURES

Various embodiments of the presently disclosed surgical instrument are disclosed herein with reference to the drawings, wherein:

FIG. 1 is a perspective view of an embodiment of a surgical instrument according to the present disclosure;

FIGS. 5-7 are side views of an end effector of the surgical instrument of FIG. 1, shown at different stages of operation;

DETAILED DESCRIPTION

Figure 1A:
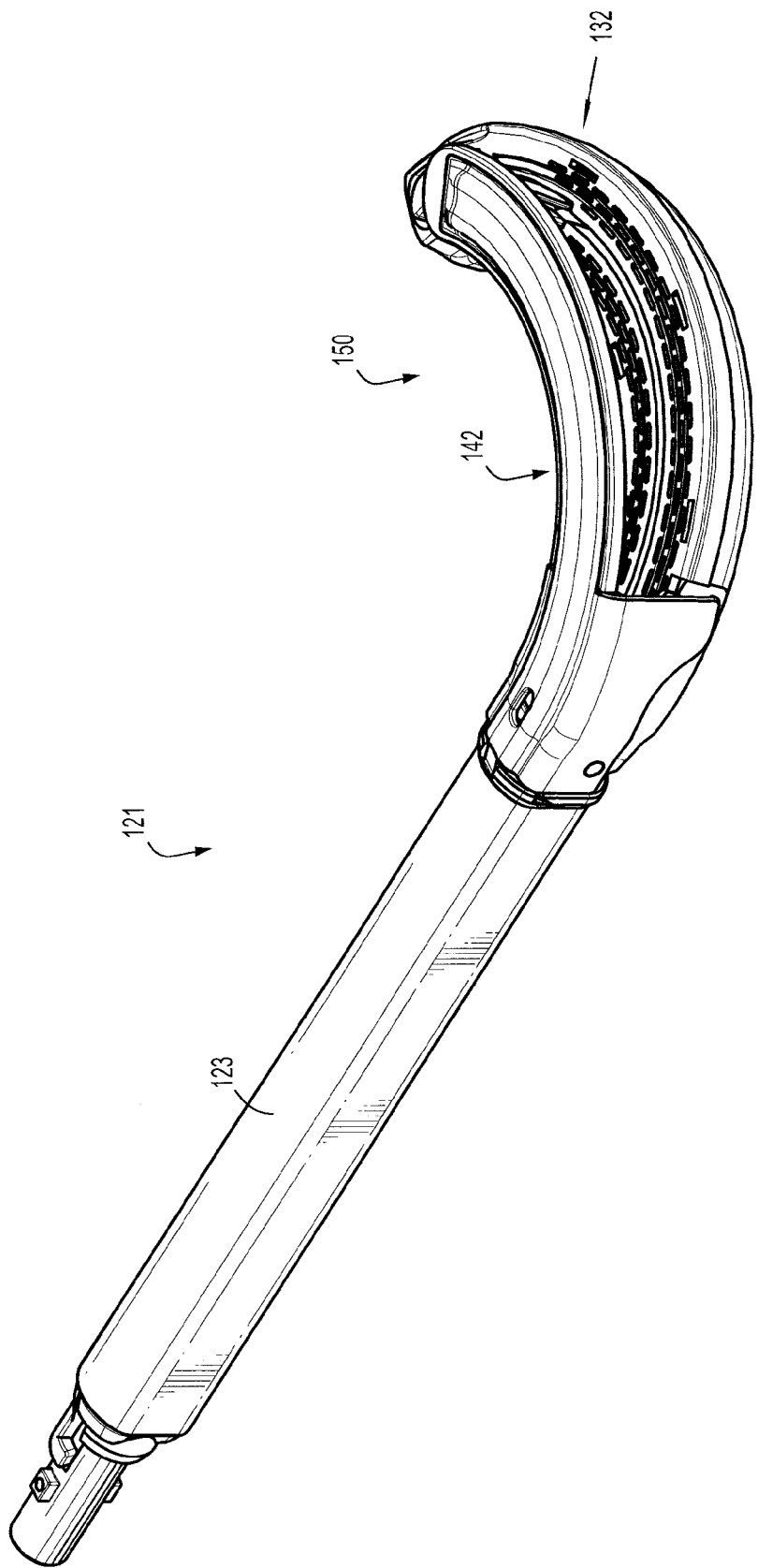
FIG. 1A is a perspective view of an embodiment of a loading unit according to certain aspects of the present disclosure.
Figure 2:
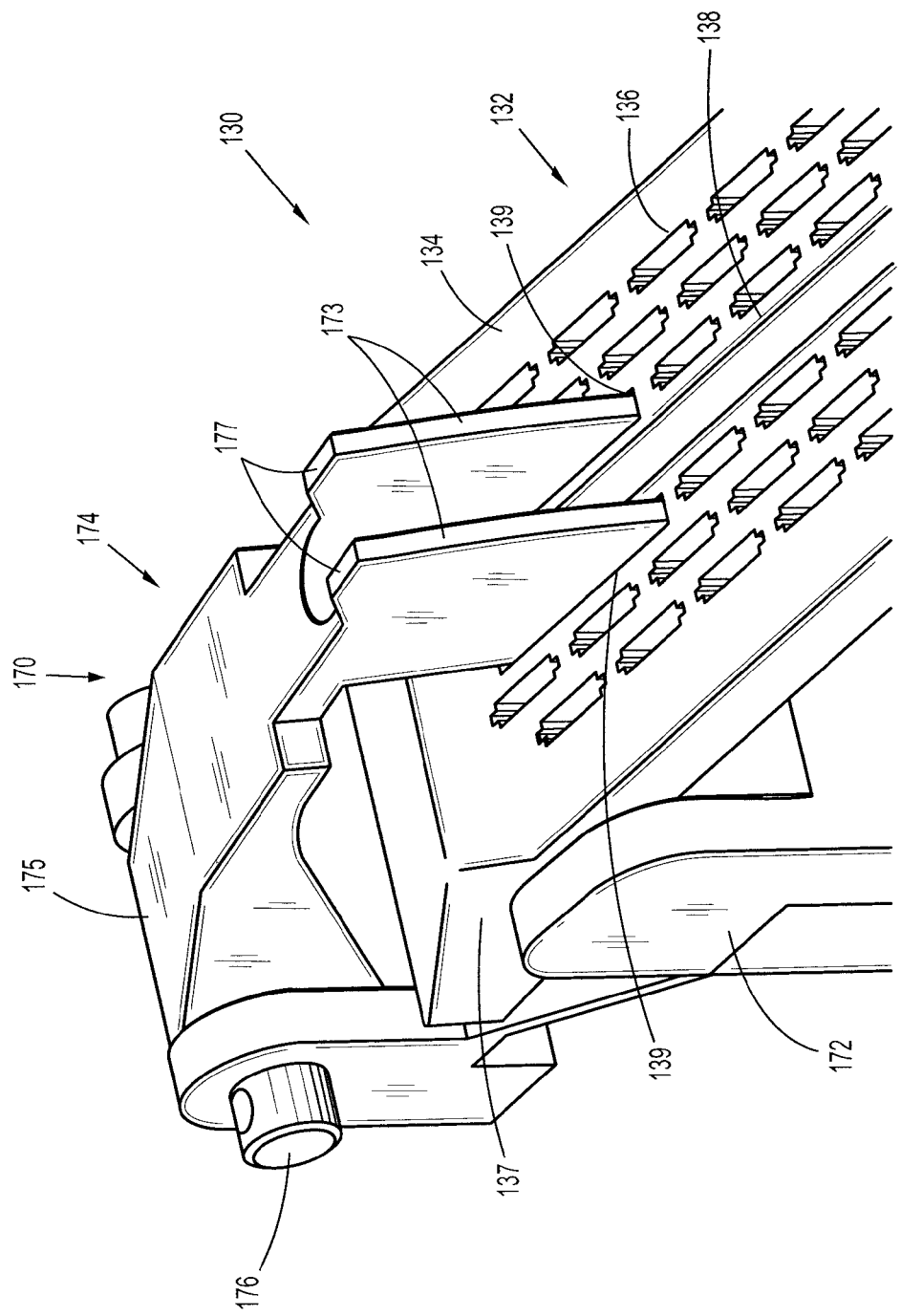
FIGS. 2-4 are perspective views of a portion of the surgical instrument of FIG. 1, showing a stop member in a first position.
Figure 3:
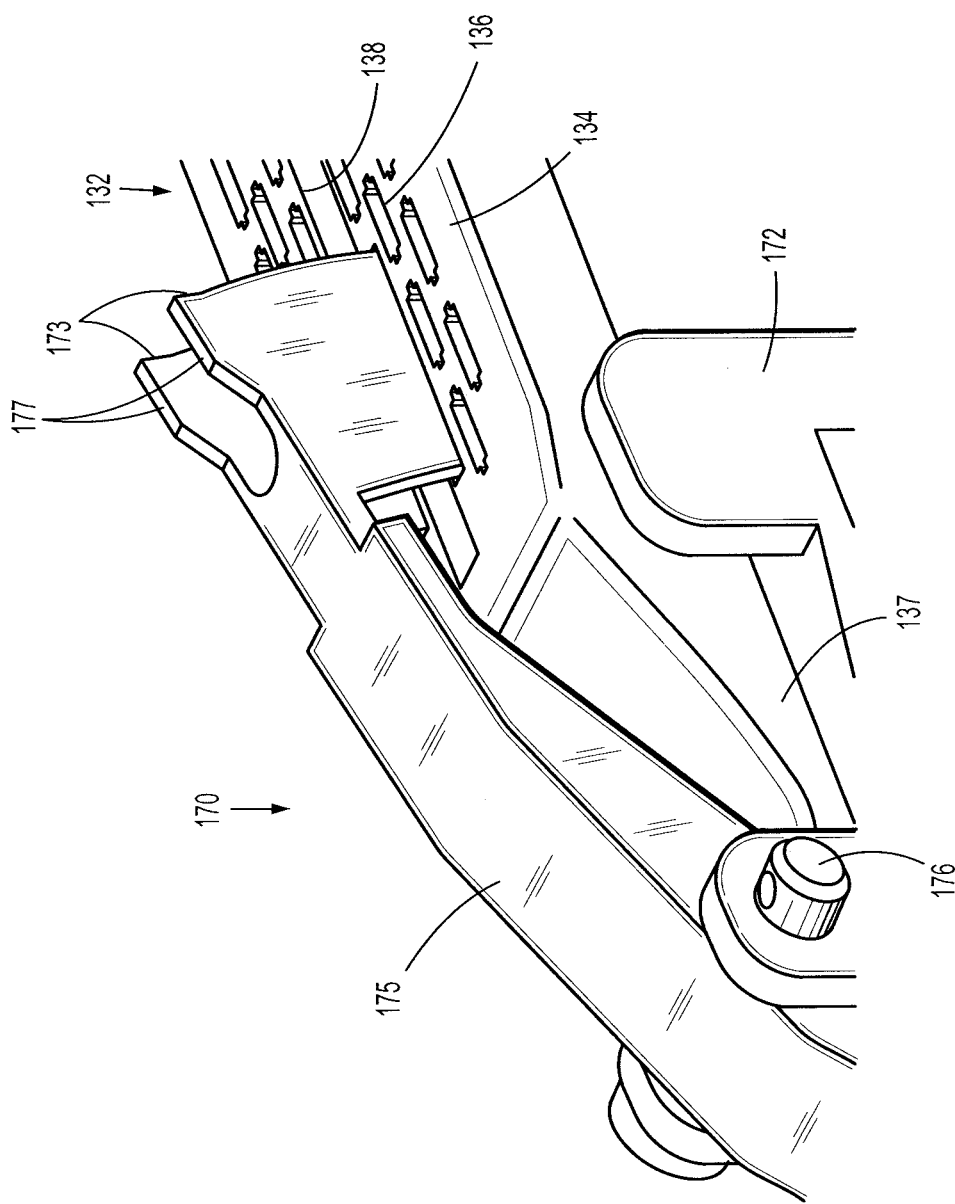
Figure 4:
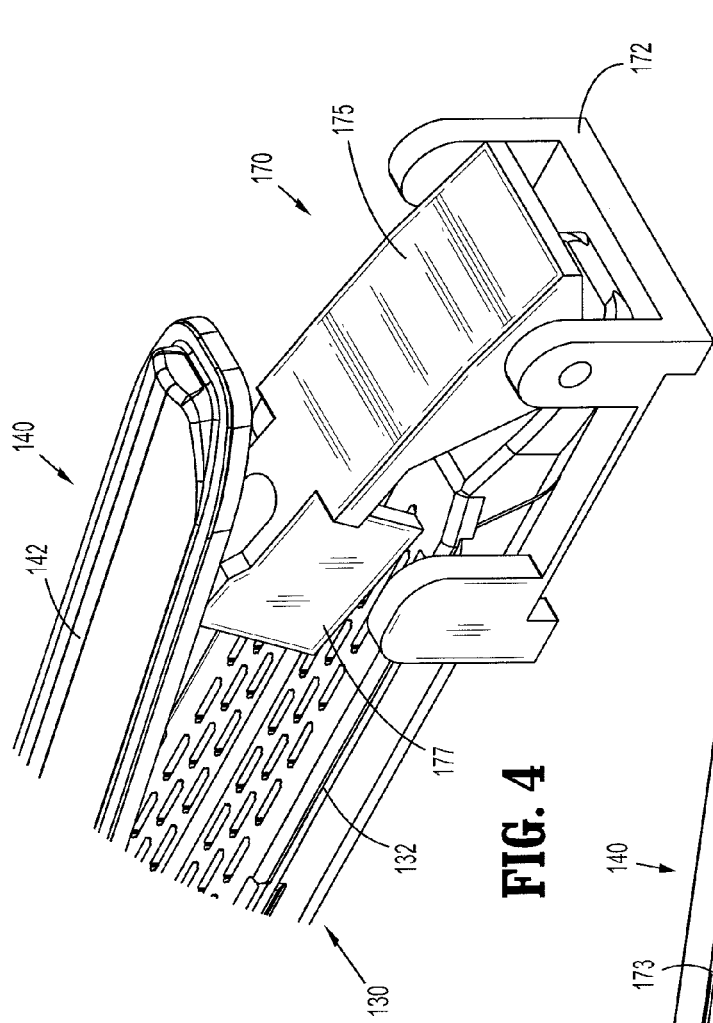

Embodiments of the presently disclosed surgical instrument are described in detail with reference to the drawings, wherein like reference numerals designate similar or identical elements in each of the several views. In the drawings and the description that follows, the term "proximal" refers to the end of the surgical instrument that is closest to the operator, whereas the term "distal" refers to the end of the surgical instrument that is farthest from the operator. As appreciated by one skilled in the art, the depicted surgical instrument fires staples, but it may be adapted to fire any other suitable fastener such as clips and two-part fasteners. Additionally, the disclosed stop member may be used with an electrosurgical forceps. Further details of electrosurgical forceps are described in commonly-owned patent application Ser. No. 10/369,894, filed on Feb. 20, 2003, entitled VESSEL SEALER AND DIVIDER AND METHOD OF MANUFACTURING THE SAME, the entire contents of which are hereby incorporated by reference herein.

With reference to FIG. 1, reference numeral 100 designates an embodiment of the presently disclosed surgical instrument. The present disclosure relates to an end effector and a stop member of surgical instrument 100. U.S. Patent Applications Publication Nos. 2008/0105730, filed on Nov. 28, 2007; 2008/0110960, filed on Jan. 8, 2008; 2008/0142565, filed on Jan. 24, 2008; 2008/0041916, filed on Oct. 15, 2007 and U.S. Provisional Patent Application Ser. Nos. 61/050273, filed on May 5, 2008 describe in detail the structure and operation of other surgical fastening assemblies. The entire contents of these prior applications are incorporated herein by reference. Any of the surgical fastening assemblies disclosed in the cited patent applications may include the presently disclosed stop member.

Surgical instrument 100 is configured to clamp, fasten, and/or cut tissue. In general, surgical instrument 100 includes a handle assembly 160, an elongate portion 120 extending distally from handle assembly 160 and defining a longitudinal axis "A-A," and a tool assembly 150 adapted to clamp and fasten tissue. Elongate portion 120 has a proximal portion 122 and a distal portion 124 and operatively couples handle assembly 160 with tool assembly 150. Tool assembly 150 includes end effector 154 and stop member 170. End effector 154, which is disposed adjacent distal portion 124 of elongated portion 120, includes a first jaw member 130 and a second jaw member 140. At least one of the jaw members 130, 140 is adapted to move relative to the other jaw member (130 or 140) between spaced and approximated positions. In the illustrated embodiment, first jaw member 130 contains a cartridge assembly 132, while second jaw member 140 includes an anvil assembly 142. The tool assembly 150 can be mounted onto the distal end of the elongate portion 120, or the tool assembly 150 can be incorporated into a replaceable loading unit 121. By way of example, FIG. 1A shows a loading unit 121 having a proximal body portion 123 that is connectable to the distal end of the elongate portion 120. This loading unit 121 includes the anvil assembly, cartridge assembly, as well as the knife and other actuation apparatus discussed below. In other examples, the tool assembly is incorporated into the surgical instrument and the cartridge assembly has a replaceable cartridge received in the first jaw member 130. The tool assembly may have linear jaws or arcuate jaws. Tool assemblies with an anvil assembly, cartridge assembly and actuation apparatus with a knife are disclosed in U.S. patent application Ser. No. 12/235,751, filed Sep. 23, 2008 and U.S. patent application Ser. No. 12/553, 174, filed Sep. 3, 2009, the disclosures of which are hereby incorporated by reference herein.

As discussed below, the anvil assembly 142 shown in FIG. 1 moves with respect to cartridge assembly 132 between spaced and approximated positions upon actuation of handle assembly 160, for example. However, the cartridge assembly may move toward and away from the anvil assembly to clamp tissue. It is also envisioned that other methods of approximating the jaw members are also usable, including sliding a clamp bar 168.

Handle assembly 160 includes a stationary handle 162 and a movable handle 164. Movable handle 164 is adapted to move pivotally toward or away from stationary handle 162. Further, movable handle 164 is operatively connected to anvil assembly 140 through a mechanism adapted to convert at least a partial actuation of movable handle 164 into a pivoting motion of at least one of cartridge assembly 132 and anvil assembly 142 between spaced and approximated positions. As recognized by one skilled in the art, any conventional actuation mechanism may be employed to operatively couple movable handle 164 to tool assembly 150.

With reference to FIGS. 2-5, cartridge assembly 132 has a tissue-contacting surface 134 and a plurality of fastener retaining slots 136. The anvil assembly 142 includes an anvil plate 143. Tissue-contacting surface 134 generally faces the anvil plate 143 on anvil assembly 142 (see FIG. 1) and, during operation, engages tissue when the anvil assembly 142 is approximated with cartridge assembly 132. Fastener retaining slots 136 are arranged in rows along tissue contacting surface 134. Each fastener retaining slot 136 is adapted to hold a fastener (not shown), such as a staple or other surgical fastener, until a user actuates handle assembly 160 (see FIG. 1), for example. When movable handle 164 is pivoted toward stationary handle 162, the fasteners are ejected from fastener retaining slots 134, move toward anvil assembly 142, and are formed in staple forming recesses in the anvil plate 143. The fasteners can be stainless steel, titanium, or other deformable surgical metal staples, polymeric staples, two-part fasteners or other surgical fasteners.

In addition to fastener retaining slots 134, cartridge assembly 132 has a knife channel 138 adapted to slidably receive a knife (not shown) or any other suitable cutting tool. Knife channel 138 is disposed between rows of fastener retaining slots 136 and extends along tissue-contacting surface 134. In operation, a knife (not shown) slides through knife channel 138 when movable handle 164 pivots toward stationary handle 162. Alternatively, other mechanisms can be used to drive the knife through knife channel 138. In addition to knife channel 138, cartridge assembly 132 has a pair of slots 139 formed on tissue-contacting surface 134. Each slot 139 provides access to an inner portion of cartridge assembly 132 and is configured to receive portions of stop member 170.

In disclosed embodiments, handle assembly 160 contains an actuation mechanism for deploying the fasteners from fastener retaining slots 136 and advancing a knife along knife channel 138. This actuation mechanism includes a firing rod operatively connected to movable handle 164. In operation, pivoting movable handle 164 toward stationary handle 162 causes firing rod to advance distally. Firing rod is in turn operatively coupled to an axial drive assembly at least partially positioned within tool assembly 150. Axial drive assembly is configured to move distally in response to a distal translation of firing rod. The axial drive assembly includes a beam that has an upper portion for engaging the anvil assembly and a lower portion for engaging the cartridge assembly. As the axial drive assembly translates distally through the anvil assembly and cartridge assembly, the engagement of the upper portion and lower portion causes the second jaw member 140 to pivot toward first jaw member 130. In addition, the axial drive assembly pushes an actuation sled disposed within first jaw member 130 in a distal direction, while the actuation sled translates distally through end effector 154. As the actuation sled advances distally through first jaw member 130, this actuation sled urges the fasteners out of the fastener retaining slots 136. In certain embodiments, axial drive assembly includes a blade mounted on a distal portion thereof. In operation, this knife moves through knife channel 138 of the cartridge assembly 132 when axial drive assembly moves distally through end effector 154. Likewise, the anvil plate 143 of the anvil assembly 142 defines a slot to allow translation of the axial drive assembly. The knife blade faces distally in the tool assembly 150 so that tissue between the jaws of the tool assembly 150 is progressively cut as the fasteners are formed.

Figure 5:
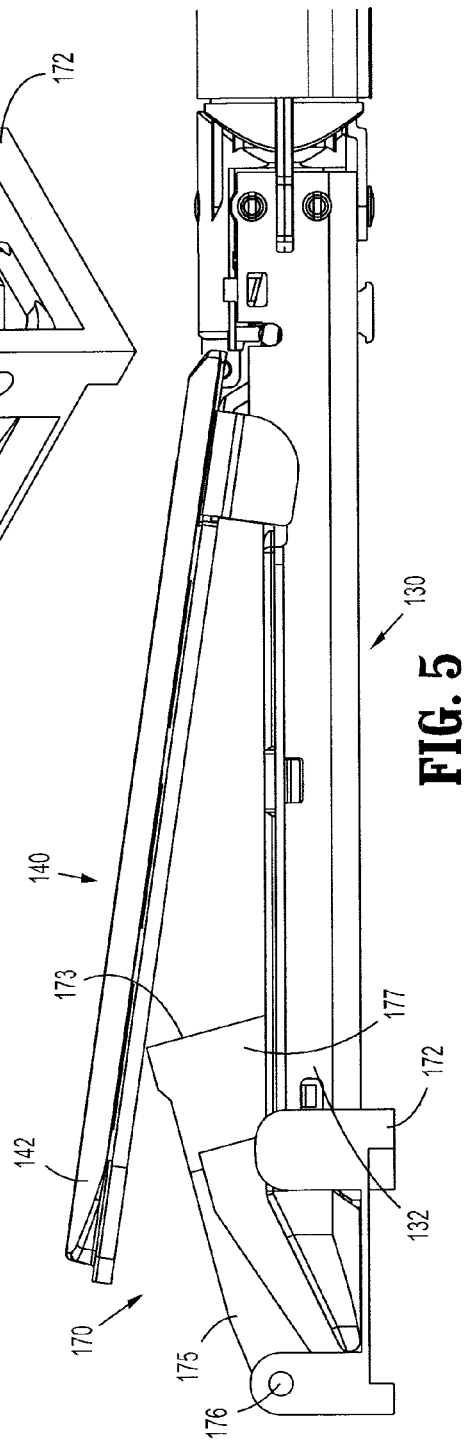

Stop member 170 is disposed adjacent a distal portion 137 of first jaw member 130 (which is shown as cartridge assembly 132, but may also be anvil assembly 142). The stop member 170 is pivotable with respect to the first jaw member 130 between a first position, as illustrated in FIG. 5, and a second position, as depicted in FIG. 7. In the first position, at least a portion of stop member 170 is located external to the first jaw member 130, whereas, in the second position, at least a portion of stop member 170 is positioned at least partially below tissue-contacting surface 134 of first jaw member 130. In various embodiments, a significant portion of stop member 170 is disposed external to the first jaw member 130 when stop member 170 is located in the first position. It is envisioned that the term "significant" means that at least half of each leg 177 of stop portion 170 is disposed external to the first jaw member 130 when stop member 170 is located in the first position. Additionally, as used herein, "significant" may mean that more than one-third of stop member 170 is disposed external to the first jaw member 130 when stop member 170 is located in the first position Stop member 170 includes a base 172 adapted to engage an outer surface of distal portion 137 of first jaw member 130 and a stopping portion 174 adapted to engage tissue. A pivot pin 176, or any other suitable apparatus, pivotally connects stopping portion 174 to base 172. Consequently, stopping portion 174 is configured to pivot away and toward tissue-contacting surface 134. In one embodiment, stop member 170 includes a biasing member (e.g., a spring) for biasing stopping portion 174 away from first jaw member 130.

Stopping portion 174 contains a body 175 and at least one leg 177 extending proximally from body 175. In the embodiment depicted in FIG. 2, stopping portion 174 has two legs 177 extending proximally from body 175. Stopping portion 174 may nonetheless include more or fewer legs 177. The two legs 177 shown in FIG. 2 define a space therebetween adapted to receive a knife. Each leg 177 is dimensioned to be received within a slot 139 and includes a proximal surface 173. When stop member 170 is located in the first position, each proximal surface 173 defines an oblique angle relative to tissue-contacting surface 134, as seen in FIG. 5. Conversely, when stop member 170 is located in the second position (see FIG. 7), each proximal surface 173 defines an angle substantially perpendicular to tissue-contacting surface 134. Irrespective of the position of stop member 170, legs 177 are shown positioned on opposite sides of knife channel 138. Slots 139, which are dimensioned to receive legs 177, are accordingly located on opposite sides of knife channel 138 as well.

Figure 8:
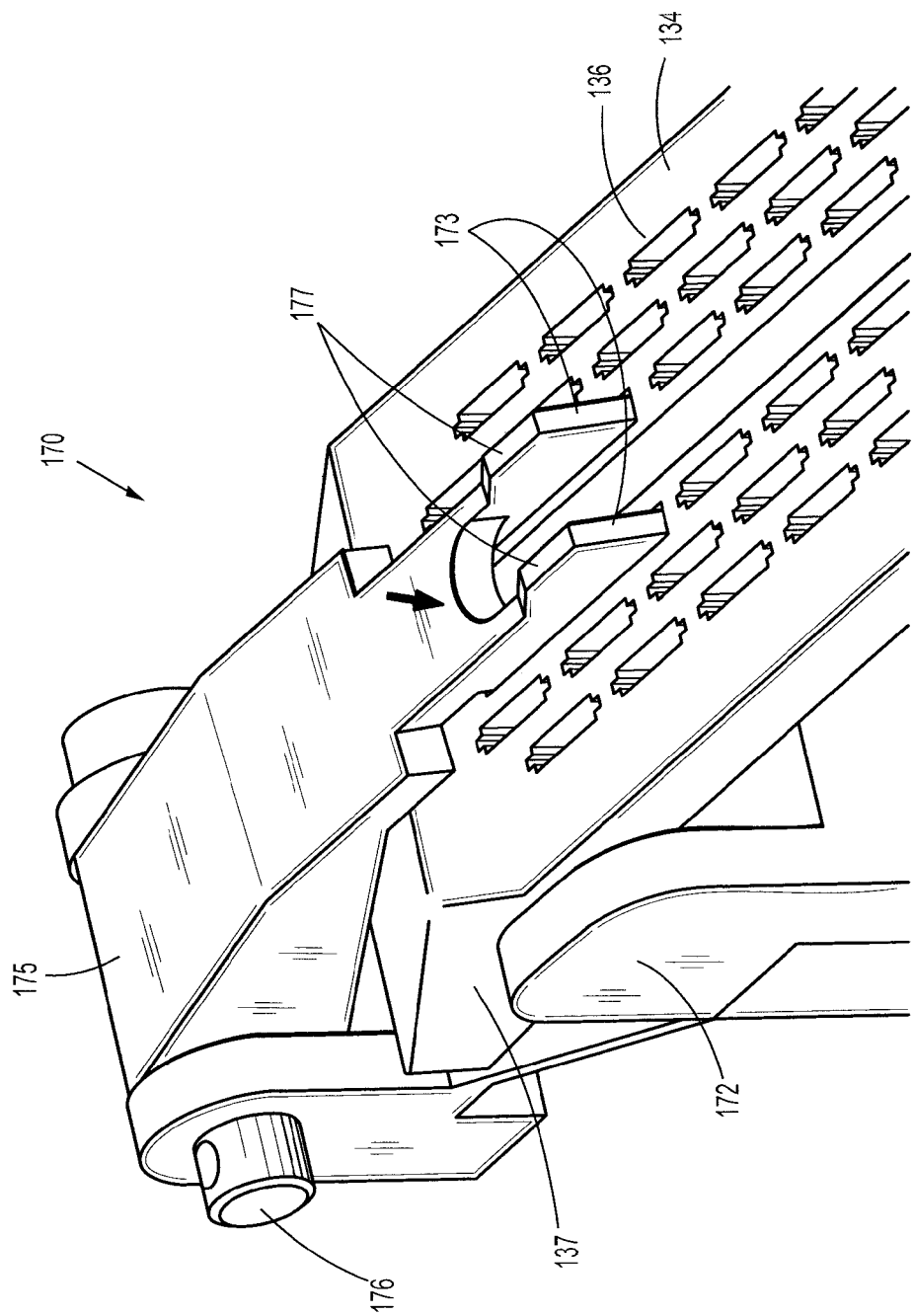
FIG. 8 is a perspective view of a portion of the surgical instrument of FIG. 1, showing a stop member adjacent its second position.

Referring to FIGS. 6-8, stop member 170 facilitates retention of tissue between first and second jaw members 130, 140 during the operation of surgical instrument 100. (See FIG. 1). That is, stop member 170 helps prevent tissue from migrating or translating distally past its intended placement between the jaw members. In use, a user initially positions surgical instrument 100 adjacent a target tissue. Particularly, the target tissue is placed between first and second jaw members 130, 140. The angle defined by body 175 relative to tissue-contacting surface 136 facilitates introduction of the target tissue "T" into tool assembly 150 in the general direction of arrow "A," as seen in FIG. 6. Once the user has placed at least a portion of the target tissue between first and second jaw members 130, 140, the user pulls movable handle 164 toward stationary handle 162 to approximate anvil assembly 152 toward cartridge assembly 132. While the user pulls movable handle 164, anvil assembly 152 moves closer to cartridge assembly 132 and the target tissue "T" is captured between tissue-contacting surface 134 of cartridge assembly 132. At the same time, anvil assembly 142 urges stopping portion 174 toward cartridge assembly 132. In response to the force exerted by the anvil assembly 142 on stopping portion 174, stopping portion 174 pivots about pivot pin 176 toward cartridge assembly 132, e.g., against the bias of biasing member (not shown). While stopping portion 174 moves closer to cartridge assembly 132, at least a portion of legs 177 move to an inner portion of cartridge assembly 132 through slots 139, as seen in FIG. 7. When stop member 170 is in the second position (as shown in FIG. 7), a portion of legs 177 is located within cartridge assembly 132; correspondingly, a portion of proximal surfaces 173 is located outside of cartridge assembly 132. As discussed above, proximal surfaces 173 define a substantially orthogonal angle relative to tissue-contacting surface 134 when stop member 170 is in the second position, thereby hindering the escape of tissue during clamping.

The present disclosure also contemplates stop member 170 being releasably attachable to end effector 150 via conventional mechanical means, e.g., bayonet coupling, latch, detent or snap-fit connection.

With reference to FIGS. 9-12, a first jaw member 230 according to another embodiment is envisioned. First jaw member 230 of this embodiment has a curved shape (i.e., with respect to longitudinal axis "A-A"). The first jaw member may be part of a loading unit including an anvil assembly, or some other surgical fastening device. It is envisioned that curved jaw members may facilitate performing certain types of surgical procedures. For example, curved jaw members, as compared to straight jaw members (such as the jaw members illustrated in FIG. 1), may help facilitate access to lower pelvic regions, e.g., during lower anterior resection ("LAR") or other colo-rectal surgery.

First jaw member 230 includes an opening 239 (FIG. 10) adapted to receive both legs 277 of stop portion 270 instead of two slots 139 each capable of receiving a leg 177 of stop member 170. Stop member 270 is similar to stop member 170. However, stop member 270 has a stopping portion 274 directly connected to a distal portion 237 of first jaw member 230. Distal portion 237 contains a hole 235 (FIG. 10) adapted to receive a pivot pin 276. Pivot pin 276, or any other suitable apparatus, pivotally couples stop member 270 to first jaw member 230.

The term "distal" typically refers to that part or component of the instrument that is farther away from the user. As used herein, the terms "distal" and "proximal" will take into account the curvature of curved parts of the surgical instrument 10 of the present disclosure. For example, "distal" will refer to the portion of the curved part that is farthest from the user, along a trajectory defined by the curved part, such as trajectory C-C shown in FIG. 12. That is, while an intermediate portion of a curved part may be farther from the user during use, the portion of the curved part that is farthest along its longitudinal axis is considered "distal."

In general, first jaw member 230 includes a curved housing 231 and a curved cartridge assembly 232. Housing 231 has a curved channel 233 adapted to receive curved cartridge assembly 232. Curved cartridge assembly 232 contains a tissue-contacting surface 234 configured to engage tissue, rows of fastener retaining slots 236 extending along its curved profile, and a knife channel 238 adapted to slidably receive a knife (not shown). Knife channel 238 is disposed between the rows of fastener retaining slots 236.

As discussed above, actuating handle assembly 160 not only ejects the fasteners, but also drives a knife along knife channel 238 (e.g., via a single stroke or multiple strokes of movable handle 164). Knife channel 238 leads to an opening 239 formed on distal portion 237 of cartridge assembly 232. A recess 280 is positioned distally of opening 239 and includes an inclined wall 282 (see FIG. 11) defining an oblique angle relative to tissue-contacting surface 234 and is adapted to receive a portion of stop member 270 therein. In addition to inclined wall 282, recess 280 has a cavity 284 adapted to receive a portion of stop member 270 (see FIG. 11).

Figure 9:
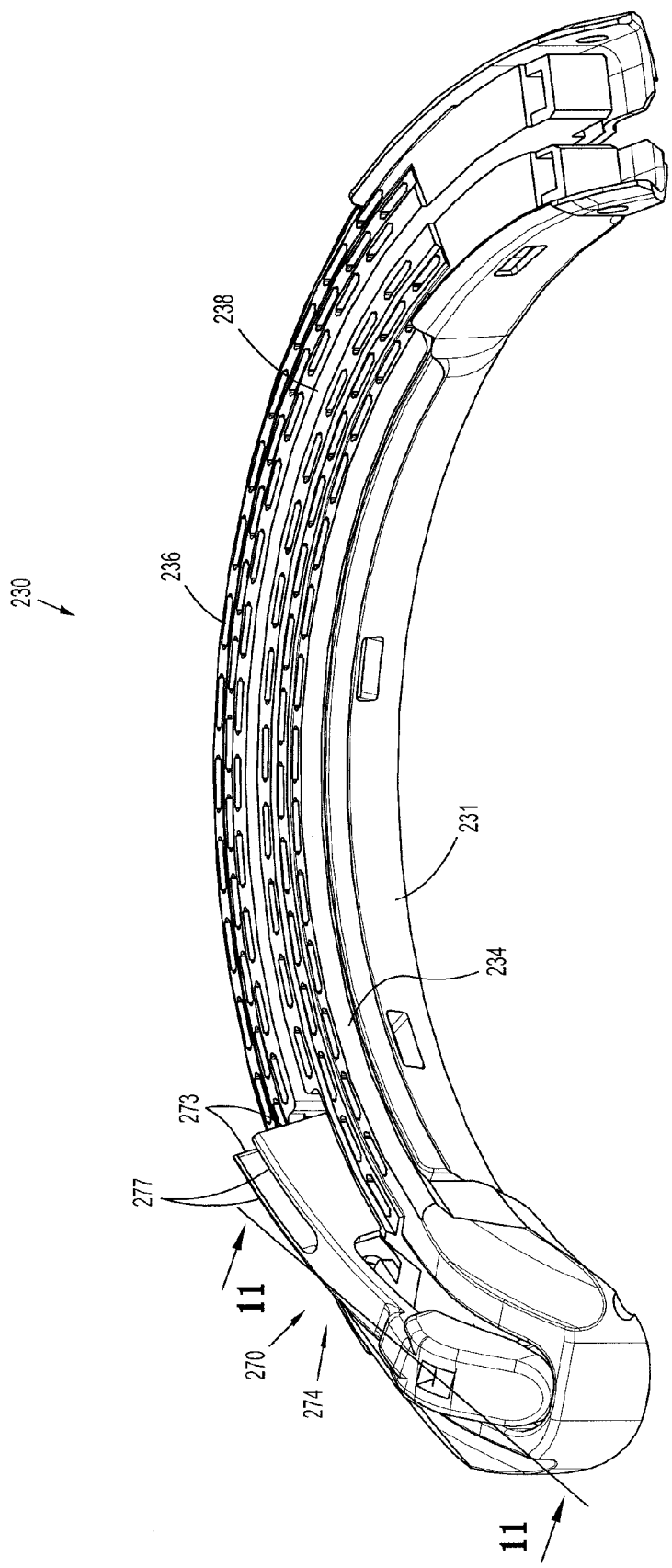
FIG. 9 is a perspective view of a curved jaw member according to another embodiment of the present disclosure, showing a stop member in a first position.
Figure 10:
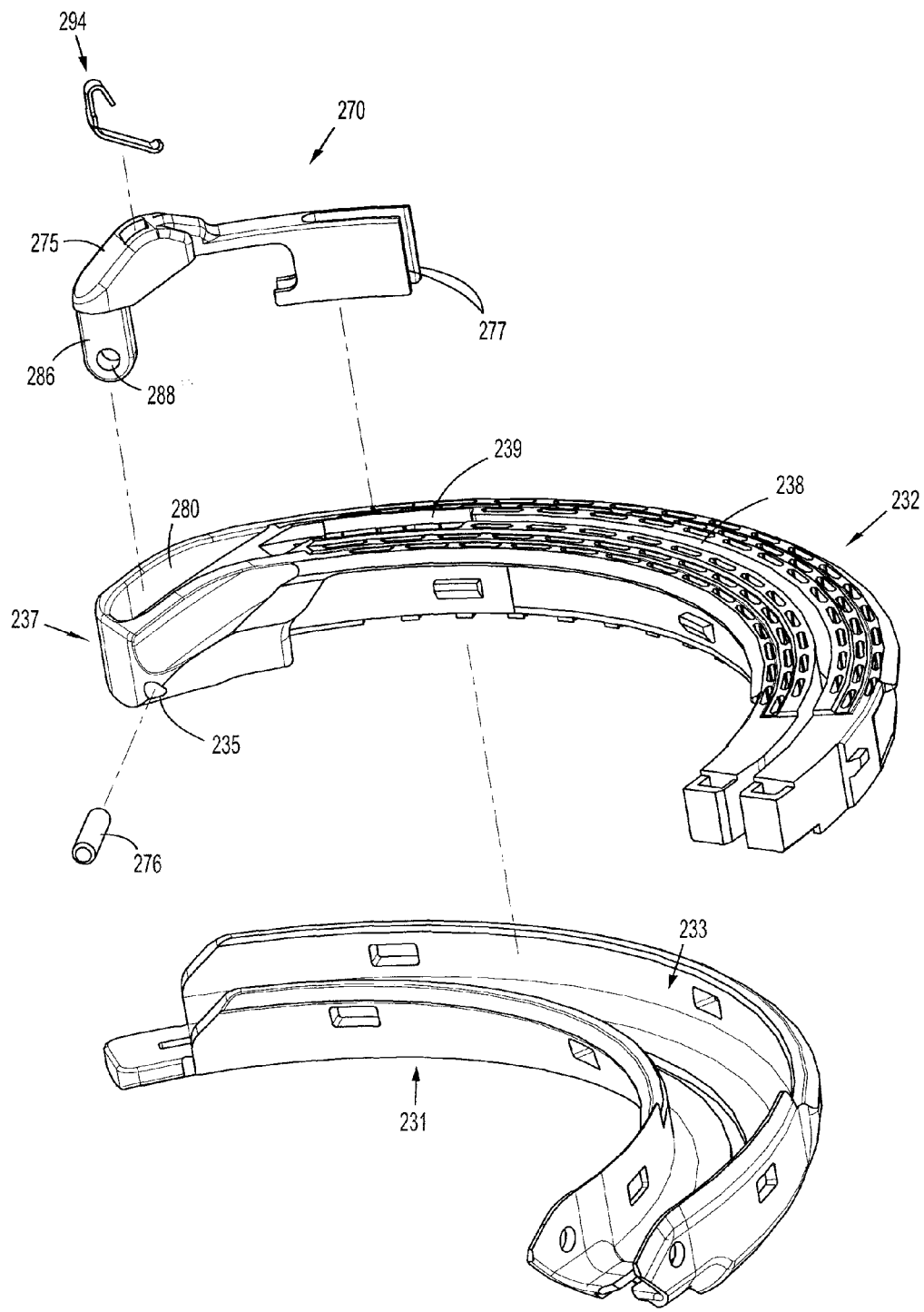
FIG. 10 is a perspective exploded view of the curved jaw member of FIG. 9.
Figure 12:
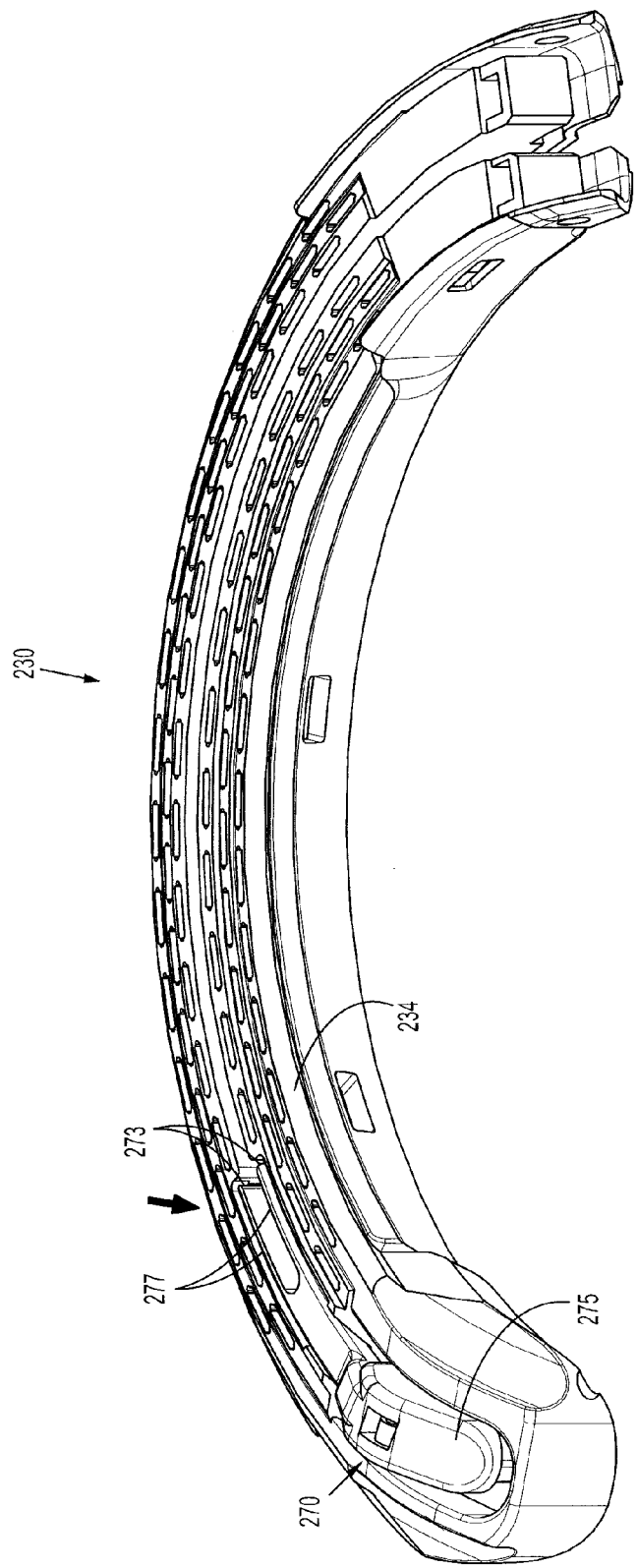
FIG. 12 is a perspective view of the curved jaw member of FIG. 9, showing the stop member in a second position.

Stop member 270 includes a body 275, a pair of legs extending proximally from body 275, and a pivoting protrusion 286 extending transversely from body 275. Legs 277 define a space therebetween dimensioned to receive a knife. Each leg 277 has a proximal surface 273 that defines an oblique angle relative to tissue-contacting surface 234 when stop portion 270 is in the first position, as shown in FIG. 9, and a substantially perpendicular angle relative to tissue-contacting surface 234 when stop portion 270 is in the second position, as illustrated in FIG. 12.

Body 275 defines an oblique angle with respect to the tissue-contacting surface 234. Pivoting protrusion 286 of stop member 270 is adapted to be received within cavity 284 and has a hole 288 configured to receive pivot pin 276. Pivot pin 276 extends through hole 235 of cartridge assembly 270 and hole 280 of pivoting protrusion 286 and allows stop member 270 to pivot from a first position where at least a portion of the stop member 270 is positioned external to first jaw member 230, as seen in FIG. 9, and a second position where at least a portion of stop member 270 is positioned at least partially below a tissue-contacting surface 234 of the first jaw member 230, as seen in FIG. 12.

Figure 11:
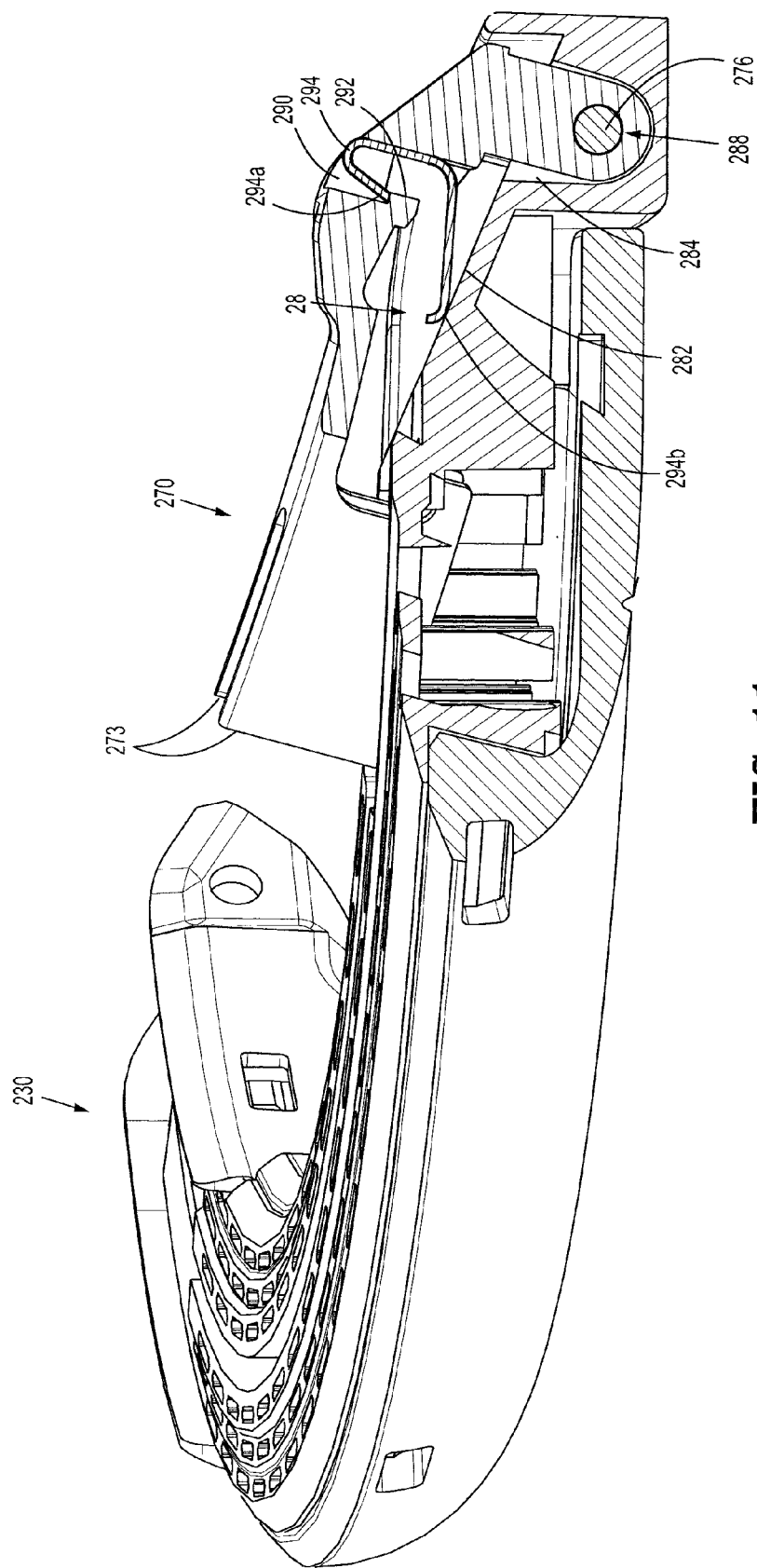
FIG. 11 is a perspective view of the curved jaw member of FIG. 9, showing the cross-section of a distal portion taken along section line 11-11 of FIG. 9.

As seen in FIG. 11, body 275 additionally contains a thru-hole 290 leading to inclined wall 282 and an abutment wall 292 protruding toward thru-hole 290. Abutment wall 292 is configured to hold a first end 294a of a biasing member 294, and inclined wall 282 is adapted to support a second end 294b of biasing member 294. Biasing member 294 biases stop member 270 towards its first position. In the embodiment depicted in FIGS. 10 and 11, biasing member 294 is a spring, but biasing member 294 can alternatively be any suitable apparatus or means capable of biasing stop member 270 away from first jaw member 230.

The operation of first jaw member 230 is substantially similar to the operation of first jaw member 130. First jaw member 230 works jointly with an anvil assembly to cut and/or fasten tissue. As a user actuates handle assembly 160, the jaw members approximate, which urges stop member 230 from the first position (see FIG. 9) to a second position (see FIG. 12). In the first position, the orientation of stop member 230 facilitates the introduction of tissue between first jaw member 230 and an anvil assembly. Further, stop member 230 inhibits tissue from distally escaping the tool assembly when stop member 230 is oriented in its second position. When the anvil assembly moves away from first jaw member 230, stop member 230, under the influence of biasing member 294, returns to its first position.

Figure 13:
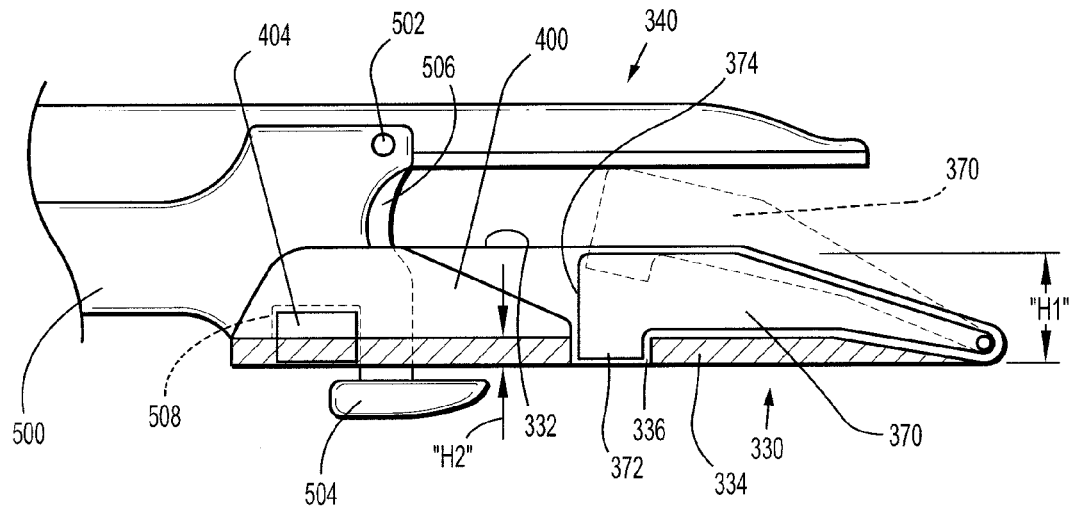
FIG. 13 is a longitudinal cross-sectional view of a distal portion of jaw members and a stop member in accordance with another embodiment of the present disclosure.
Figure 14:
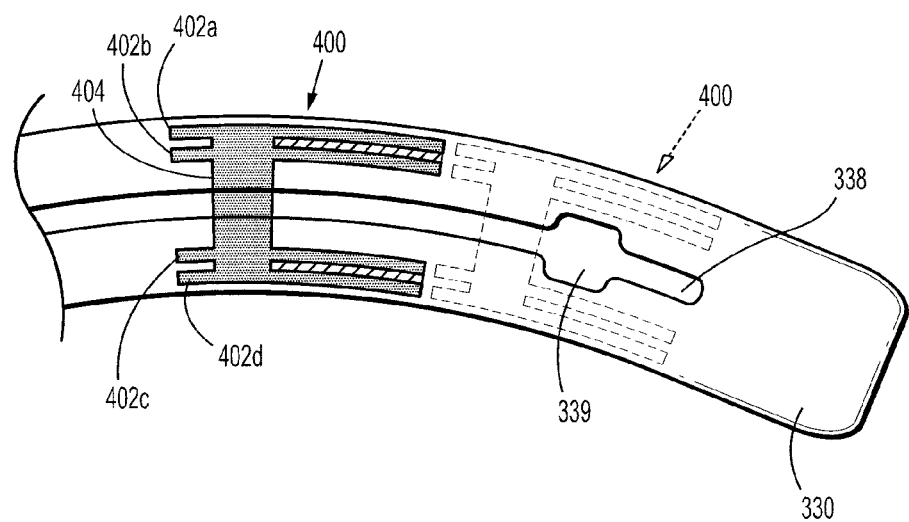
FIG. 14 is a top view of the jaw members of FIG. 13, with the stop member omitted.

FIGS. 13-14 illustrate another embodiment of a first jaw member 330, and a second jaw member 340 for a surgical stapling instrument. Another embodiment of a tissue stop 370 is illustrated in FIG. 13. FIG. 13 illustrates tissue stop 370 in its first, initial position (phantom lines) and in its second position (solid lines). Similar to the embodiments disclosed hereinabove, tissue stop 370 is biased towards its initial position, and in approximation of the jaw members, contact with the opposing jaw member causes tissue stop 370 to move towards its second position. By way of example, the first jaw member 330 is a staple cartridge assembly, and the second jaw member 340 is an anvil assembly. Other surgical instrument jaws, such as electrosurgical, are contemplated.

With particular reference to FIG. 13, first jaw member 330 (e.g., cartridge assembly) includes an upper tissue-contacting surface 332 and a lower shelf portion 334. Lower shelf portion 334 includes a groove 336 extending at least partially therethrough. As shown in FIG. 13, groove 336 is configured to accept a portion of tissue stop 370 therein. In particular, groove 336 is configured to accept a lip 372 of tissue stop therein. Groove 336 enables tissue stop 370 to include a stopping portion 374 having a maximum height "H1." More particularly, tissue stop 370 is configured to fit within first jaw member 330 (i.e., not protrude above upper tissue-contacting surface 332, and not protrude below lower shelf portion 334) when tissue stop 370 is in its second position (i.e., corresponding to first and second jaw members 330, 340, respectively, being approximated with respect to one another), and to extend between the tissue-contacting surface 332 and the anvil plate when the tissue stop 370 is in its first position (such as when the first jaw member and second jaw member are spaced from one another and ready to receive tissue). Thus, without the inclusion of groove 336, the maximum height of stopping portion 374 would be decreased by the height "H2" of lower shelf portion 334. As can be appreciated, the greater the height "H1" of stopping portion 374, the increased ability surgical instrument has to contain thicker tissue between the jaw members. That is, the relatively large height "H1" of stopping portion 374 helps prevent a greater amount of tissue (e.g., a greater thickness of tissue) from distally escaping the jaw members.

Figure 15:
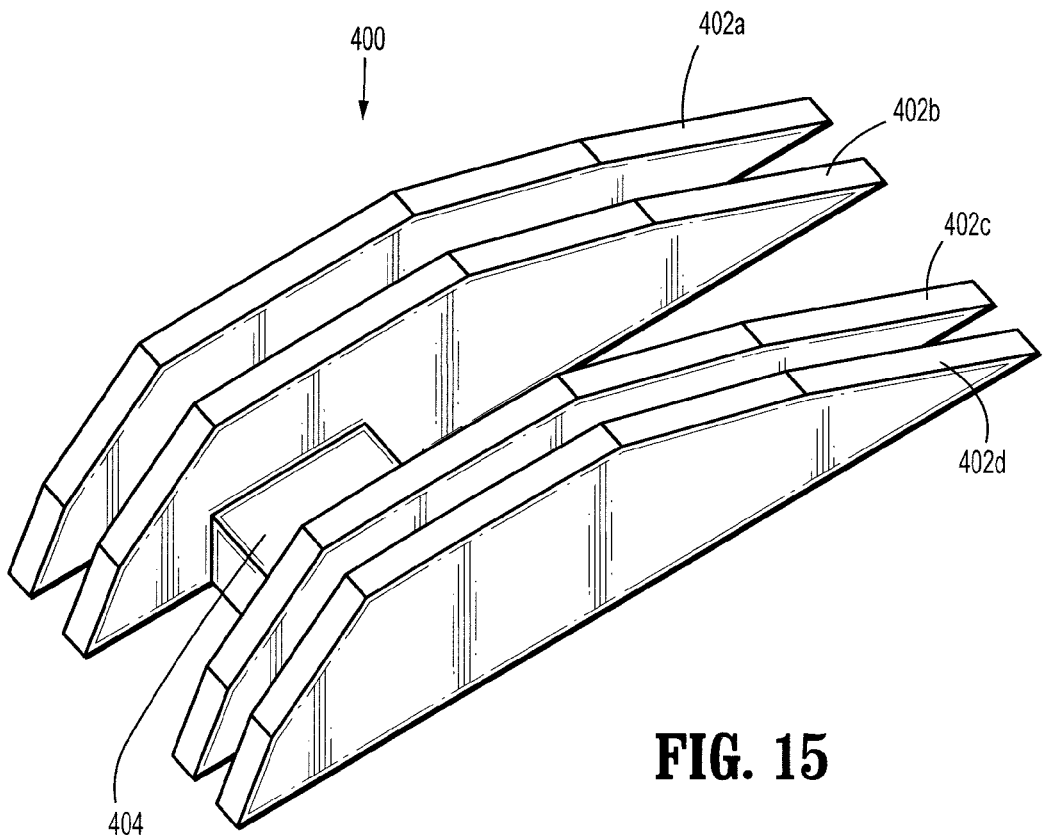
FIG. 15 is a perspective view of a sled for use with the embodiment of the jaw members illustrated in FIGS. 14 and 15.

An actuation sled 400 is illustrated in FIGS. 13-15. Actuation sled 400 is longitudinally translatable (including along a curved path) with respect to first jaw member 330 (e.g., cartridge assembly). As discussed above, an axial drive assembly pushes actuation sled 400 in a distal direction, and as actuation sled 400 advances distally through and along lower shelf portion 334 of first jaw member 330, actuation sled 400 urges fasteners out of the fastener retaining slots. For example, a beam including a knife may be used to advance the actuation sled to fire the fasteners.

In the illustrated embodiments, actuation sled 400 includes four cam wedges 402a, 402b, 402c, and 402d and a transversely-extending connecting member 404 which operably connects each cam wedge with its adjacent cam wedge(s). As illustrated, connecting member 404 is proximally disposed with respect to each cam wedge 402. The proximal location of connecting member 404 with respect to cam wedges 402 creates distal portions of each of cam wedge 402 that are elongated and that cantileveredly extend from connecting member 404. It is also envisioned that portions (e.g., distal portions) of wedge 402a are connected to adjacent wedge 402b, and that portions of wedge 402c are connected to adjacent wedge 402d via connecting member 404 and/or a separate member, to enhance stability of actuation sled, for instance. The present disclosure also includes an actuation sled 400 including more or fewer than the illustrated four cam wedges.

Actuation sled 400 is configured to accommodate tissue stop 370, and in particular, lip 372 of tissue stop 370. In particular, the proximal orientation of connecting member 404 enables distal portions of cam wedges 402 to contact fasteners or pusher members (not explicitly illustrated in FIGS. 13-15) that are distally disposed within first jaw member 330 without interfering with lip 372 of tissue stop 370. More specifically, when actuation sled 400 is in its distal-most position (as illustrated by the phantom lines in FIG. 14), connecting member 404 is positioned proximally of lip 372 of stop member 370 (location of lip 372 is indicated by a widened portion 339 of a knife channel 338 in FIG. 14), thus enabling distal portion of cam wedges 402 to cause ejection of the most distally-disposed fasteners (not shown). While the distal-most portion of cam wedges 402 is illustrated as being substantially aligned with the distal edge of knife channel 338 when actuation sled 400 is in a distal position, it is envisioned that the distal-most portion of cam wedges 402 extends proximally of and/or distally beyond the distal edge of knife channel 328.

Referring back to FIG. 13, an I-beam assembly 500 is illustrated in connection with first jaw member 330 and second jaw member 340. According to the embodiment illustrated in FIG. 13, I-beam assembly 500 generally includes an upper member 502 configured to slidably engage a slot in second jaw member 340, a lower member 504 configured to slide beneath lower shelf portion 334 of first jaw member 330, and a knife 506 configured to cut tissue between the jaw members 330, 340. Additionally, I-beam assembly 500 also includes a notch 508 along a lower surface thereof which is configured to mechanically engage connecting member 404 of actuation sled 400. As such, distal approximation of the I-beam assembly 500 results in approximation of the jaw members 330, 340, results in cutting of tissue between the jaw members 330, 340, and also results in distal advancement of actuation sled 400, which causes fasteners to be ejected from first jaw member 330. In certain embodiments, the knife 506 is disposed between legs 277 of the tissue stop, the legs defining a recess for receiving the knife 506. A plastic, compressible and/or elastic material may be disposed in the recess defined by the legs 277 for pressing tissue against the knife 506, at the end of travel for the I beam assembly 500. Additionally, retraction of I-beam assembly 500 in a proximal direction causes a corresponding proximal retraction of actuation sled 400. It is also envisioned that when I-beam assembly 500 is proximally retracted to a predetermined location, at least one jaw member moves towards the open position with respect to the other jaw member.

Figure 16:
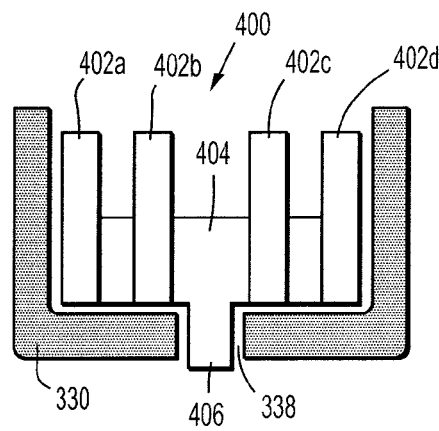
FIG. 16 is a transverse cross-sectional view of a portion of jaw member of FIG. 14 and a sled in accordance with another embodiment of the present disclosure.

With reference to FIG. 16, a transverse cross-sectional view of a portion of jaw member 330 and sled 400 is shown. In this embodiment, connecting member 404 is shown with an alignment nub 406 downwardly depending therefrom. Alignment nub is configured to follow the curvature of the knife channel 338 as the actuation sled 400 translates with respect to the jaw member 330. The engagement between the alignment nub 406 and the knife channel 338 may help maintain the relative lateral position (e.g., centered) of the actuation sled with respect to the jaw member 330 during translation of the actuation sled 400.

It will be understood that various modifications may be made to the embodiments of the presently disclosed surgical instruments. Therefore, the above description should not be construed as limiting, but merely as exemplifications of embodiments. Those skilled in the art will envision other modifications within the scope and spirit of the present disclosure.

What is claimed is:

1. A surgical instrument for surgically joining tissue, the surgical instrument comprising:
   an end effector having a first jaw member and a second jaw member, at least one of the first jaw member and the second jaw member being movable with respect to the other jaw member, the first jaw member being a staple cartridge assembly having a tissue contacting surface and a groove, a sled member being disposed in a staple cartridge of the staple cartridge assembly; and
   a stop member disposed adjacent a distal portion of the staple cartridge assembly, the stop member being configured to impede tissue from distally escaping the jaw members;
   the sled member being configured to accommodate a portion of the stop member.

2. The surgical instrument of claim 1, wherein at least one of the jaw members is curved, and wherein the stop member is pivotable with respect to the first jaw member between a first position where a portion of the stop member is external to the groove, and a second position where a portion of the stop member is positioned at least partially within the groove.

3. The surgical instrument of claim 2, further comprising a biasing member disposed in mechanical cooperation with the stop member, wherein the biasing member biases the stop member towards its first position.

4. The surgical instrument of claim 2, wherein the stop member is pivotally coupled to the first jaw member.

5. The surgical instrument of claim 1, wherein at least one jaw member includes a knife channel.

6. The surgical instrument of claim 5, wherein the stop member further comprises a first leg and a second leg, the first leg and the second leg being positioned on opposite sides of the knife channel.

7. The surgical instrument of claim 1, further comprising an I-beam assembly.

8. The surgical instrument of claim 7, wherein the I-beam assembly has a notch, the I-beam assembly engaging a connecting member of the sled member at the notch.

9. A surgical instrument for surgically joining tissue, the surgical instrument comprising:
   an end effector having a first jaw member and a second jaw member, at least one of the first jaw member and the second jaw member being movable with respect to the other jaw member, the first jaw member being a staple cartridge assembly having a tissue contacting surface and a groove, a sled member being disposed in a staple cartridge of the staple cartridge assembly; and
   a stop member disposed adjacent a distal portion of the staple cartridge assembly, the stop member being configured to impede tissue from distally escaping the jaw members;
   the sled member being configured to accommodate a portion of the stop member, wherein the stop member has a lip, the sled member being configured to accommodate the lip.

10. The surgical instrument of claim 9, wherein the sled member includes a connecting member that is positioned at a proximal portion of the sled member.

* * * * *